United States Patent [19]
Bird et al.

[11] Patent Number: 5,326,502
[45] Date of Patent: Jul. 5, 1994

[54] PYRIDYLBENZIMIDAZOLE COMPOSITIONS FOR ABSORBING ULTRAVIOLET LIGHT

[75] Inventors: George R. Bird, Princeton, N.J.; Louis Locatell, Chico, Calif.; Kenneth S. Norland, Lexington; Louis M. Scarmoutzos, Andover, both of Mass.

[73] Assignee: Steadfast, Incorporated, Cambridge, Mass.

[21] Appl. No.: 561,930

[22] Filed: Aug. 2, 1990

[51] Int. Cl.⁵ .................... F21V 9/04; C07F 9/80; C07D 487/00
[52] U.S. Cl. .................... 252/589; 252/588; 546/2; 546/271; 548/314.7
[58] Field of Search .................... 546/2, 271; 548/327; 252/589, 587, 588

[56] References Cited

U.S. PATENT DOCUMENTS 4,188,486 2/1980 Tsukamoto et al. .................... 546/271

OTHER PUBLICATIONS

Chemical Abstracts, 104715M, vol. 67, 1967 (Leshshenko et al. Zh. Obshch. Khim., 37(5), pp. 1069–1073 (1967)).

Leshenko et al., Zhurnal. Obsch. Khim., vol. 37, No. 5, pp. 1069–1073, (1967).

*Primary Examiner*—Philip Tucker
*Attorney, Agent, or Firm*—Wolf, Greenfield & Sacks

[57] ABSTRACT

Metal complexes of pyridylbenzimidazoles are described which can be used as ultraviolet absorbers. The pyridylbenzimidazole compounds can be substituted or unsubstituted. The ultraviolet absorbers can be used to protect a carrier or to protect objects being shielded by a carrier.

36 Claims, 2 Drawing Sheets

5,326,502

PYRIDYLBENZIMIDAZOLE COMPOSITIONS FOR ABSORBING ULTRAVIOLET LIGHT

FIELD OF THE INVENTION

The present invention relates to compositions capable of absorbing ultraviolet light, particularly compositions containing an effective amount of a metal complex of a pyridylbenzimidazole compound and a carrier.

BACKGROUND

Ultraviolet light is emitted by the sun, carbon arc lamps, mercury vapor lamps, tungsten lamps and other light sources. The ultraviolet portion of the spectrum is from about 180 to about 390 nm. Ultraviolet light having a wavelength within this range is capable of degrading synthetic resins or polymers presently used to manufacture structures, or coatings commonly exposed to ultraviolet light, e.g., sidings, paints, or varnishes.

It is estimated that over 40% of all plastics in the United States need some protection from ultraviolet radiation. A polymeric matrix can be photochemically broken down causing discoloration, cracking, embrittlement and peeling. Ultraviolet photodegradation can result in the loss of optical, physical, and mechanical properties of the original polymer.

There is a need for improved ultraviolet absorbers because some presently available ultraviolet absorbers are subject to ultraviolet degradation themselves, i.e. they are not stable as ultraviolet absorbers for long periods of time when incorporated in a carrier.

SUMMARY OF THE INVENTION

This invention pertains to metal complexes of pyridylbenzimidazole compounds and compositions for absorbing ultraviolet light containing at least one of such complexes. The compositions of this invention contain an effective amount of at least one metal complex of a pyridylbenzimidazole compound and a carrier. The compositions of the present invention may further comprise other known absorbers for providing enhanced absorption. Known absorbers is intended to include art-recognized absorbers known to absorb light at a particular wavelength. The preferred metal complexes of this invention are those of the following formula:

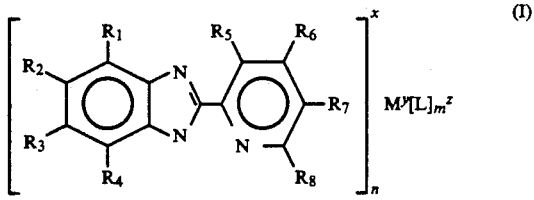

wherein M is a metal; L is a ligand; n is a number between 1 and 4; m is a number betwen 0 and 4; $R_1$-$R_8$ are each independently selected from the group consisting of hydrogen, hydroxyl, alkyl, alkenyl, alkynyl, aryl, aralkyl

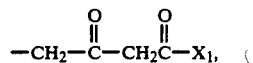

substituted or unsubstituted benzimidazoyl, carboxylic acids, carboxylic esters and amides, —$SO_3H$, —$SO_2X_1$; alkylphenols, alkylphenol ethoxylates, halogen, haloalkyl, —$NX_2$, and —$OX_3$, wherein $X_1$ is alkyl, alkenyl, aryl, aralkyl, alkynyl; wherein $X_2$ is hydrogen, oxygen, alkyl, alkenyl, aryl, aralkyl or alkynyl; $X_3$-is hydrogen, alkyl, alkenyl, alkynyl, aryl, aralkyl,

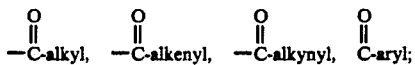

and x, y, and z are the electrical charges associated with each moiety.

According to this invention an advantageous ultraviolet light absorber comprises an organic chromophore capable of absorbing ultraviolet light energy and linked to at least one metal ion. The ultraviolet light energy is passed to the metal ion which dissipates the ultraviolet light energy absorbed by the chromophore by passing the energy to a surrounding area in the form of heat.

This invention further pertains to a method for protecting a material from ultraviolet light by combining an effective amount of a pyridylbenzimidazole metal complex with the carrier. The protected material can be the carrier and/or a material in the carrier or an underlying object or surface.

This invention also pertains to novel pyridylbenzimidazole metal complexes having the formula depicted in formula I above wherein at least one of the $R_1$-$R_8$ moieties is not hydrogen.

It is an object of this invention to provide an ultraviolet absorber which is stable with regard to its ability to absorb ultraviolet light for prolonged periods of time when compared to known ultraviolet absorbers.

It is an object of this invention to provide an ultraviolet absorber which is soluble in different types of carriers or compatible therewith.

It is another object to provide ultraviolet absorbers which do not substantially degrade when exposed to ultraviolet light.

It is still another object of this invention to provide ultraviolet light absorbers which contain organic chromophores and metal portions, which metal portions catalyze the dissipation of ultraviolet light absorbed as heat to surrounding areas.

DETAILED DESCRIPTION

Figure 1:
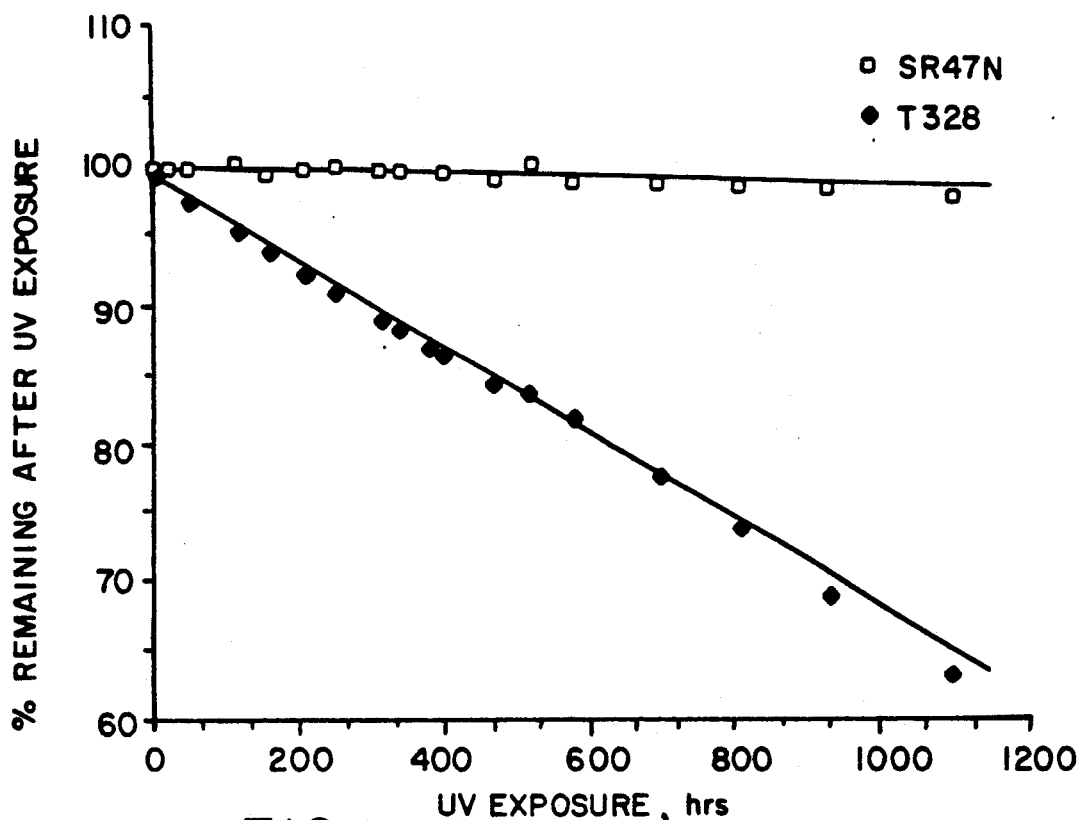
FIG. 1 is a graph showing the stability of a $Ni^{+2}$ complex of 2-( 2-pyridyl )benzimidazole/triphenylphosphine sulfide complex (SR47N) and a 2-(3,5-tert-amyl-6-hydroxyphenyl )benzotriazole (Tinuvin 328) as absorbers of ultraviolet light. Cellulose acetate butyrate was used as the carrier.

This invention pertains to metal complexes of pyridylbenzimidazole compounds and compositions for absorbing ultraviolet light comprising an effective amount of a metal complex of a pyridylbenzimidazole compound and a carrier. An effective amount is that amount necessary for absorbing a significant portion of the ultraviolet light being transmitted to or through the carrier. Examples of effective amounts of metal complexes include from about 0.1 to about 3 percent by weight or more.

The pyridyl moiety of the pyridylbenzimidazole compound can be attached at any position which is sterically possible. The preferred pyridylbenzimidazole compounds are the substituted or unsubstituted forms of 2-(2-pyridyl)benzimidazoles, 7-(2-pyridyl)benzimidazoles, 4-(2-pyridyl)benzimidazoles, and 2,6-bis-(2-benzimidazyl)pyridines. Substituents which can be used on either the pyridyl or benzimidazoyl moieties include those listed for the $R_1$-$R_8$ moieties described above.

Preferred metal complexes of this invention have the following formula:

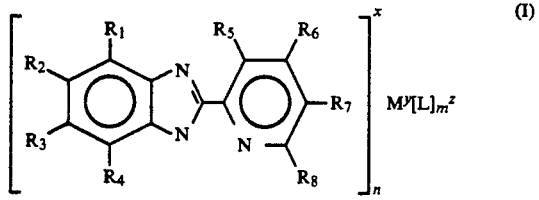

wherein M is a metal; L is a ligand; n is a number between 1 and 4; m is a number between 0 and 4; $R_1$-$R_8$ are each independently selected from the group consisting of hydrogen, hydroxyl, alkyl, alkenyl, alkynyl, aryl, aralkyl

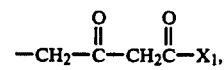

substituted or unsubstituted benzimidazoyl, carboxylic acids, carboxylic esters, amides, —$SO_3H$, —$SO_2X_1$; alkylphenols, alkylphenol ethoxylates, halogen, haloalkyl, —$NX_2$, and —$OX_3$, wherein $X_1$ is alkyl, alkenyl, aryl, aralkyl, alkynyl; wherein $X_2$ is hydrogen, oxygen, alkyl, alkenyl, aryl, aralkyl or alkynyl; $X_3$ is hydrogen, alkyl, alkenyl, alkynyl, aryl, aralkyl,

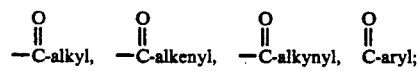

and x, y, and z are the electrical charges associated with each moiety. In formula (I), a hydrogen may be associated with the nitrogen at the No. 1 or 3 position of the benzimidazole group or the benzimidazole group may carry a negative charge in place of the hyrdrogen. Even though Formula I is depicted without a hydrogen, the formula is intended to encompass both situations for purposes of this invention. Examples of species of pyridylbenzimidazole compounds which can be used within this invention are depicted in Table I below.

TABLE I

| Cpd No. | $R_1$ | $R_2$ | $R_3$ | $R_4$ | $R_5$ | $R_6$ | $R_7$ | $R_8$ | Ni II complex Max$\lambda_{MeOH}$ (nm) | Max$\lambda_{MeOH}$ (nm) |
|---|---|---|---|---|---|---|---|---|---|---|
| 1 | H | H | H | H | H | H | H | H | 323 | 308 |
| 2 | H | H | H | H | OH | H | H | H | 341 | 326 |
| 3 | H | H | $NO_2$ | H | H | H | H | H | 344[a] | 329 |
| 4 | H | H | $NH_2$ | H | H | H | H | H | 359[a] | 344 |
| 5 | H | H | O‖C—Ph | H | H | H | H | H | 354[b] | 328 |
| 6 | H | H | H | H | $OCH_2Ph$ | H | H | H | 347[a] | 332 |
| 7 | H | H | H | H | (1) | H | H | H | 327[a] | 312 |
| 8 | H | H | O‖C—Ph | H | OH | H | H | H | 346 | 333 |
| 9 | Cl | Cl | Cl | Cl | H | H | H | H | 330 | 314 |
| 10 | Cl | Cl | Cl | Cl | OH | H | H | H | 368[b] | 333 |
| 11 | H | H | H | H | H | H | H | benzimidazoyl | 344[a] | 329 |
| 12 | H | H | H | H | H | H | H | substituted benzimidazoyl | 344[a] | 329 |
| 13 | H | (2) | H | H | H | H | H | H | | |
| 14 | H | (3) | H | H | H | H | H | H | 334[c] | 321[a] |
| 15 | Cl | Cl | Cl | Cl | $OCH_3$ | H | H | H | | |
| 16 | Cl | Cl | Cl | Cl | $OCH_2Ph$ | H | H | H | | |
| 17 | Cl | Cl | Cl | Cl | (1) | H | H | H | | |
| 18 | H | H | H | H | $OCH_3$ | H | H | H | | |
| 19 | H | H | H | H | $OCH_2Ph$ | H | H | H | | |
| 20 | H | H | H | H | (1) | H | H | H | | |
| 21 | Cl | (4) | Cl | Cl | H | H | H | H | | |
| 22 | Cl | (5) | Cl | Cl | H | H | H | H | | |

TABLE I-continued

[Structure: benzimidazole-pyridine compound with substituents $R_1$-$R_8$]

| Cpd No. | $R_1$ | $R_2$ | $R_3$ | $R_4$ | $R_5$ | $R_6$ | $R_7$ | $R_8$ | Ni II complex Max$\lambda_{MeOH}$ (nm) | Max$\lambda_{MeOH}$ (nm) |
|---|---|---|---|---|---|---|---|---|---|---|
| 23 | H | (6) | H | H | H | H | H | H | | |
| 24 | Cl | (6) | Cl | Cl | H | H | H | H | | |
| 25 | H | (4) | H | H | H | H | H | H | | |
| 26 | H | (5) | H | H | H | H | H | H | | |

(1) $\overset{O}{\overset{\|}{O}}C-CH(CH_2CH_3)(CH_2)_3CH_3$
(2) $c\text{-}C_6H_{11}$
(3) $n\text{-}C_{14}H_{29}$
(4) $-O\ Ar-(CH_2)_8CH_3$
(5) $O-(CH_2CH_2O)_n-O-Ar-(CH_2)_8CH_3$
n = 2, 5, or 12
(6) $-NHC\overset{O}{\overset{\|}{-}}\overset{Et}{\overset{|}{CH}}-nBu$ $^a$estimated
$^b$DMSO solvent (dimethylsulfoxide)
$^c$CH$_2$Cl$_2$ solvent Metals which can be used in the complex of the present invention include Ni, Ti, Zn, Mn, Co, V, Sn, Pb, Fe, Cr, and Cu. The metals are preferably di- or trivalent. Transition metals are preferred, e.g. Ni, Mn, Co, Cr, Fe, and Cu.

The terms alkyl, alkenyl and alkynyl are intended to include branched or straight chained alkyl, alkenyl, alkynyl, or aryl and aralkyl groups. Examples of alkyls, alkenyl or alkynyl groups which can be used in this invention of those having from about 1 to about 14 carbon atoms, e.g., methyl, ethyl, ethenyl, ethynyl, propyl, propenyl, propynyl and tetradecyl.

The term aryl includes phenyl and multiple ring systems, e.g. napthyl. The term aralkyl includes aryl as defined above substituted with hydrocarbon moieties, e.g alkyl, alkenyl or alkynyl groups.

The sum of the electrical charges associated with each moiety, x, y and z, preferably is equal to zero. The net charge, however, can be positive or negative with the counter ions in the solvent or carrier neutralizing the complex.

The term halogen is intended to encompass the elements listed in Group VII of the periodic table. Examples of halogens include Cl, Br, F and I.

The term haloalkyl includes alkyl groups wherein at least one of the hydrogen atoms is replaced with a halogen substituent. Examples of haloalkyls include CF$_3$, CHF$_2$, CH$_2$F, CCl$_3$, CHCl$_2$ and CH$_2$Cl.

The metal complexes of this invention may be dissolved in an organic or inorganic solvent, such as water, dimethylsulfoxide, mineral spirits, hexane, methanol, ethanol, and methylene chloride. The solvent may be in addition to the carrier or the solvent may be the carrier, e.g. a plastic or varnish.

The term ligand is intended to include both solubilizing and photostabilizing agents. The ligand may also be both a solubilizing and a stabilizing agent. The term solubilizing agent as used in this specification can also be an additional material which can be used in conjunction with the complex to enhance solubility in a solvent.

The composition may optionally comprise the solubilizing and/or photostabilizing agent as the ligand (L) where m>0 or a solubilizing agent can be present in the composition which is not a ligand, e.g. m can equal 0. A solubilizing agent is an agent capable of enhancing the solubility of the metal complex in the carrier or other solvent. A photostabilizing agent enhances the light stability of the metal complex in the carrier. The solubilizing/photostabilizing agent preferably is coordinated to the metal, i.e. m>0. It may or may not also absorb ultraviolet light in the same spectral region as the pyridylbenzimidazole-metal complex. Solubilizing is intended to include substantially uniform distribution such that the solvent or material containing the metal complex is substantially clear. It will also be understood that in a non-transparent medium (either a light scattering plastic or a material loaded with some solid pigment) the ultraviolet absorbing agent may, in part, exist as microscopic particles.

A compound in accordance with this invention is considered to be more light stable than another compound if, as a result of absorbing the same total dose of ultraviolet radiation, it loses less absorbance at its absorbance maximum than the second compound. The method is described in more detail below (Example 7).

The ligand selected can be beneficial to the stability or solubility of the metal complex in a particular solvent. For example, if 2-ethylhexanoic acid is used as a coordinating solubilizing agent with a nickel pyridylbenzimidazole (PBI) complex (Formula I), the carboxylate group adds to the complex as evidenced by mass spectroscopy of this compound. The resulting complex is very soluble in non-polar media such as mineral spirits and an alkyd varnish as well as in halogenated solvents such as methylene chloride. Nickel-PBI is not appreciably soluble in these media, but it is far more soluble in polar solvents, e.g., 1:1 water:methanol, than is the complex with 2-ethylhexanoic acid.

Examples of coordinating photostabilizers are triphenylphosphine sulfide and triphenylphosphine oxide.

The photostabilities of the complexes of these compounds are better than that of Nickel PBI alone by a factor of approximately five.

An example of an additional compound which can be added to the complex I and be associated with the complex, but which is not coordinated to the metal ion is a surface active agent such as benzalkonium chloride. It markedly enhances (greater than ten times) the photostabilities of Nickel-PBI complexes in cellulose acetate butyrate, with improvement in their solubilities in ethyl acetate. Benzalkonium chloride is a solubilizing and surface active agent that can be used with or without a ligand in combination with formula I in a variety of solvents.

The solubilizing agent preferably is an agent that coordinates with the metal complex and provides solubilizing and photostabilizing effects and acts as (L) in formula (I). Examples of solubilizing agents include triphenylphosphine oxide, triphenylphosphine sulfide, triphenylphosphine, and organic acids or salts thereof (Na and K, for example) such as ethylhexanoic acid, e.g. 2-ethylhexanoic acid or the sodium salt thereof. Additional solubilizing agents to supplement or replace (L) can also include surface active agents such as benzalkonium chloride. Examples of photostabilizing agents can include triphenylphosphine oxide, triphenylphosphine sulfide, and organic acids such as ethylhexanoic acid, e.g. 2-ethylhexanoic acid.

The carrier can be any material that would otherwise would be adversely affected by ultraviolet light. Examples of carriers include plastics, polymeric materials, e.g., certain types of transparent glasses, liquids, cosmetic formulations, epoxys, dyes, nitrocellulosics, paints (oil and water based), phenolics, pigments, rubber (natural or synthetic), skin and hair solutions or formulations, foodstuffs, photographic materials, synthetic fibers, urea formaldehyde resins, varnishes, films, e.g. solar control window films, wool, cellulosic material, e.g., wood or paper, or organic solvents.

Polymeric materials which can be used as carriers include organic thermoplastic and thermosetting plastics and resins. Examples of such polymeric materials include polyesters, polyethers, polyurethanes, aliphatic hydrocarbons, polyolefins, e.g., polyethylene and polypropylene, polyvinylchloride, polystyrene, acrylics, alkyds, polybutylene, polyethylene terephthalates, polycarbonates, polyacrylonitriles, polymers of the acrylonitrile/butadiene/styrene series, polybutadiene, polyvinylchloride, polyvinylidene chloride, unsaturated dicarboxylic acids, polyols, e.g., glycols, and acrylates, such as polymethylmethacrylates.

The metal complex of the pyridylbenzimidazole compound can be coated on or incorporated within the carrier using conventional techniques. The complex can be coated on the carrier by brushing, dipping, spraying or laminating. The metal complex of the pyridylbenzimidazole compound can be incorporated within the carrier by using conventional mixing, extrusion, or dipping techniques, and the like.

The pyridylbenzimidazole compounds of the present invention can be obtained by condensing a phenylenediamine with a carboxypyridine as known in the art. The condensation reaction is preferably conducted in the presence of polyphosphoric acid for about six hours at a temperature of about 180 degrees C. The phenylenediamine and carboxypyridine compounds are preferably selected to have the substituents ($R_1$-$R_8$ moieties) desired on the final compound. Alternatively, the substituents can be attached to the pyridylbenzimidazole core at a later stage in the synthesis using conventional techniques, e.g. alkylation, halogenation, etc. The positions where no substituents are desired can be blocked prior to the halogenation and or alkylation step.

The metal complex of the pyridylbenzimidazole compound can be obtained by heating a polar solution of the compound with an appropriate source of metal, e.g., a metal carboxylate. The metal source can be added alone or added in combination with the photostabilizing or solubilizing agent. The solubilizing and/or photostabilizing agent can also be added to the metal complex if the desired product is a pyridylbenzimidazole complex bound to or in association with a solubilizing and/or photostabilizing agent.

The preferred 2-(2-pyridyl)benzimidazole compounds having the following formula:

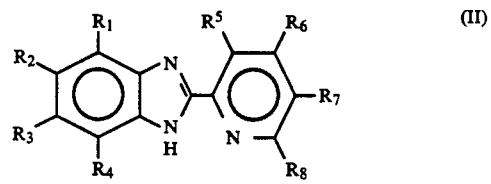

(II)

can be prepared by condensing reactant A having the formula:

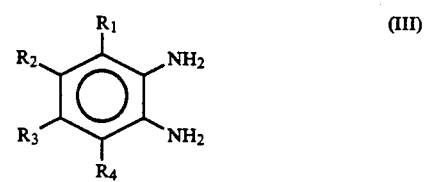

(III)

with reactant B having the formula:

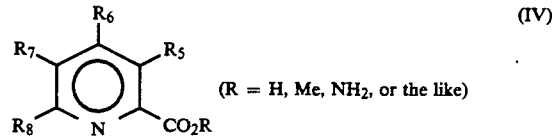

(IV)

(R = H, Me, $NH_2$, or the like)

The condensation reaction is preferably conducted at a temperature between about 180°-220° C. in the presence of poll/phosphoric acid (PPA) for a time period of about six hours. The reaction mixture is subsequently cooled and combined with near boiling distilled water. The reaction mixture/distilled water solution is stirred and filtered hot and the pH of the supernatant is adjusted to about 6 or 7. The precipitate [2-(2-pyridyl)benzimidazole] is filtered off, washed with distilled water and dried.

The metal complex of the 2-( 2-pyridyl )benzimidazole compound

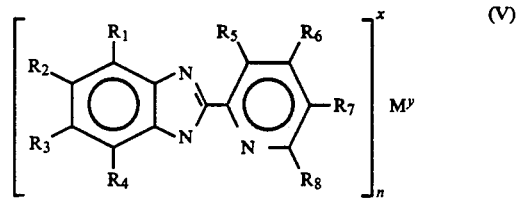

(V)

may be obtained by heating a polar solution of the 2-(2-pyridyl)benzimidazole with the appropriate metal acetate. Preferably, the metal acetate is added to the 2-(2-pyridylbenzimidazole) compound at approximately 1:1-3 molar ratio, respectively. Alternatively, the metal complex may be prepared by combining the appropriate metal source with the solubilizing and/or photostabilizing agent and this solution combined with the pyridylbenzimidazole compound.

The metal complex of the 2-(2-pyridyl)benzimidazole compounds can optionally be associated or bound to a solubilizing agent as shown in formula I.

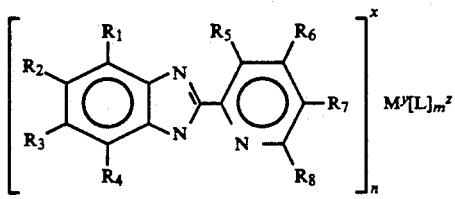

The solubilizing agent can be added to the compound of formula V prior to evaporation to dryness. Preferably, the solubilizing agent is added to the compound of formula V at a molar ratio of 1 or 2 to 1, respectively.

This invention further pertains to a method for protecting a material. The material can be an object being shielded from ultraviolet light and/or a carrier. The carrier containing the metal complex can also be protected from ultraviolet light. A carrier can be protected from ultraviolet light by combining an effective amount of a pyridylbenzimidazole metal complex with the carrier. In a method for protecting an object from ultraviolet light, the object is shielded with a carrier containing an effective amount of a pyridylbenzimidazole metal complex. The terms pyridylbenzimidazole metal complex, "an effective amount", and carrier are as defined above.

The object being shielded can be any object susceptible to undesirable effects when exposed to ultraviolet light. Examples of objects include subjects, e.g. humans, or animals, parts of a subject, e.g. skin, hair, eyes. The protected object can also be equipment, components of equipment, architectural structures, automobiles, etc.

The ultraviolet light absorbers of this invention have at least one metal ion bound to an organic chromophore. The energy absorbed by the chromophore from the ultraviolet light is passed to the metal. The metal then acts to dissipate the energy as heat to the surrounding area or carrier thus preventing decomposition and damage to the chromophore that might otherwise occur. This mechanism prolongs the life of the chromophore and enables it to act as an absorber for long periods of time. The ultraviolet light absorber has good stability over a long time period. The ultraviolet absorber comprises an organic chromophore capable of absorbing ultraviolet light energy linked to at least one metal ion. The metal ion acts to dissipate the ultraviolet light energy absorbed by the chromophore and passed to the metal ion by passing the energy to a surrounding area in the form of heat.

This invention will be better understood from the following non-limiting examples.

EXAMPLE 1—Preparation of 2-(2-pyridyl)benzimidazole

A 2 liter 3-neck round-bottom flask fitted with a reflux condenser, $N_2(g)$ inlet, mechanical stirrer, and heating mantle was charged with 88.7 g of 1,2-phenylenediamine, 100.0 g of picolinic acid, and 500 g of polyphosphoric acid. The resulting slurry was slowly heated (over a period of approximately three hours) to 210° C. under a positive nitrogen atmosphere, with mechanical stirring. The reaction mixture was heated for an additional six hours while maintaining the temperature between 200°-220° C. The reaction mixture was cooled to below 100° C. and cautiously poured into 2 liters of hot distilled water. The resulting slurry was stirred for approximately one hour, cooled and the pH adjusted to approximately 6-7 using concentrated aqueous NaOH. The slurry was stirred for an additional hour, cooled, and filtered. The precipitate was thoroughly washed with distilled water and dried.

EXAMPLE 2—Preparation of 4, 5, 6, 7-Tetrachloro-2-(2-pyridyl) benzimidazole

The 2-( 2-pyridyl )benzimidazole (10 g) prepared in Example 1 was cautiously dissolved in 400 ml. of aqua regia (300 ml. of conc. HCl and 100 ml. of conc. $HNO_3$) with cooling in an ice bath. The reaction mixture was slowly heated to reflux (100° C.) and was maintained at the reflux temperature for about three hours. The reaction mixture was cooled, poured into 1 liter of distilled water and stirred for about thirty minutes. The 4, 5, 6, 7-tetrachloro-2-(2-pyridyl)benzimidazole precipitate was filtered, thoroughly washed with distilled water, then acetone, and dried.

EXAMPLE 3—Preparation of 4, 5, 6, 7-Tetrachloro-2-(2-pyridyl) benzimidazole $Ni^{+2}$ Complex The 4,5,6,7-tetrachloro-2-(2-pyridyl )benzimidazole of Example 2 (3 g) was dissolved in 50 ml. of methanol.

A $Ni^{+2}$ acetate solution was formed by dissolving sodium acetate (0.74 g) in 20 ml. of methanol and adding this solution to a second solution of $NiCl_2.6H_2O$ (0.97 g) in 10 ml. of methanol. The reaction mixture was boiled for fifteen minutes, cooled and the precipitate was removed by filtration and the supernatant was saved. The solution of 4, 5, 6, 7-tetrachloro-2-(2-pyridyl)benzimidazole was added to the supernatant and the reaction mixture was boiled for about one hour and evaporated to dryness. The solid was triturated with diethyl ether, filtered, and the nickel complex precipitate having the following formula was washed with ether and dried.

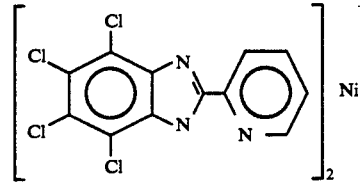

EXAMPLE 4—Preparation of 4, 5, 6, 7-Tetrachloro-2-(2-pyridyl) benzimidazole $Ni^{+2}$/Triphenylphosphine oxide Complex Prior to evaporating the precipitate of Example 3 to dryness, triphenylphosphine oxide (2.5 g in 20 ml. of methanol) was added to the reaction mixture. The reaction mixture was boiled for approximately thirty minutes, evaporated to dryness, triturated in diethyl ether, and filtered. The 4,5,6,7-tetrachloro-2-(2-pyridyl)benzimidazole $Ni^{+2}$/triphenylphosphine oxide precipitate was washed with diethyl ether and dried.

EXAMPLE 5—Preparation of 4, 5, 6, 7, Tetrachloro (2-pyridyl)benzimidazole $Ni^{+2}$/Ethylhexanoate Complex In a theoretical example, a sodium ethylhexanoate solution is prepared by dissolving 43.3 g of 2-ethyl-l-hexanoic acid and 12.0 g of NaOH in 500 ml of methanol with heating. The sodium ethylhexanoate solution is added to a solution of 35.7 g of $NiCl_2.6H_2O$ in 150 ml methanol and boiled for ~15 minutes. The $Ni^{+2}$ ethylhexanoate solution is cooled, the precipitate is removed by filtration and the supernatant is saved. A slurry of 100.0 g of 4, 5, 6, 7,-tetrachloro-( 2-pyridyl )benzimidazole in 500 ml methanol is added to the supernatant and the resulting solution is boiled with stirring for approximately 1 hour. The solution is evaporated to dryness and triturated with 1200 ml of anhydrous ether for approximately 14 hours. The precipitate is removed by filtration, washed with ether and discarded. The supernatant is saved. The supernatant is evaporated and the resulting solid is removed and dried.

EXAMPLE 6—Preparation of 2-(2-pyridyl)benzimidazole $Ni^{+2}$/Ethylhexanoate Complex A sodium ethylhexanoate solution is prepared by dissolving 164.0 ml of 2-ethyl-l-hexanoic acid and 41.1 g of NaOH in 500 ml of methanol with heating. The sodium ethylhexanoate solution is added to a solution of 122.0 g of $NiCl_2.6H_2O$ in 150 ml methanol and boiled for ~15 minutes. The $Ni^{+2}$ ethylhexanoate solution is cooled, the precipitate was removed by filtration and the supernatant was saved. A slurry of 100.0 g of 2-(2-pyridyl)benzimidazole in 500 ml methanol is added to the supernatant and the resulting solution is boiled with stirring for approximately 1 hour. The solution is evaporated to dryness and triturated with 1200 ml of anhydrous ether for approximately 14 hours. The precipitate is removed by filtration and discarded, washed with ether and the supernatant is saved. The supernatant is evaporated and the resulting solid is removed and dried.

Figure 2:
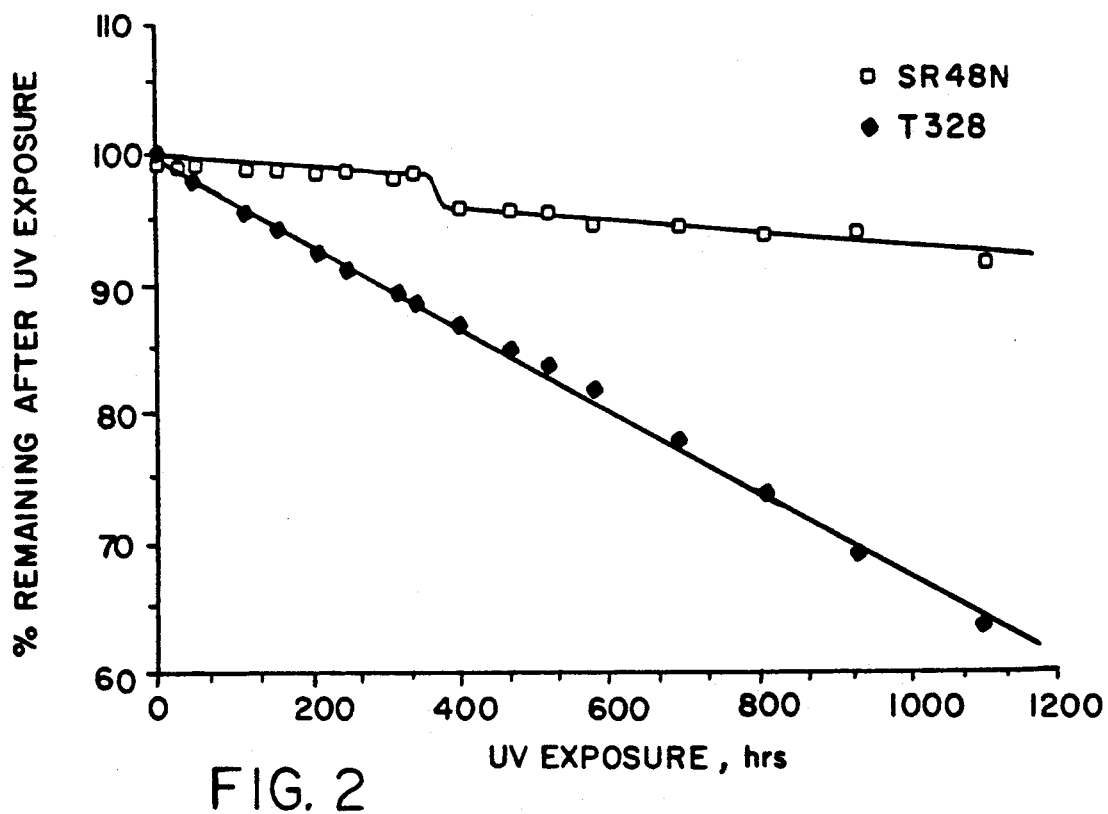
FIG. 2 is a graph showing the stability of a $Ni^{+2}$ complex of 2-( 2-pyridyl )benzimidazole/triphenylphosphine oxide complex (SR48N) and a 2-(3,5-tert-amyl-6-hydroxyphenyl )benzotriazole (Tinuvin 328) as absorbers of ultraviolet light. Cellulose acetate butyrate was used as the carrier.
Figure 3:
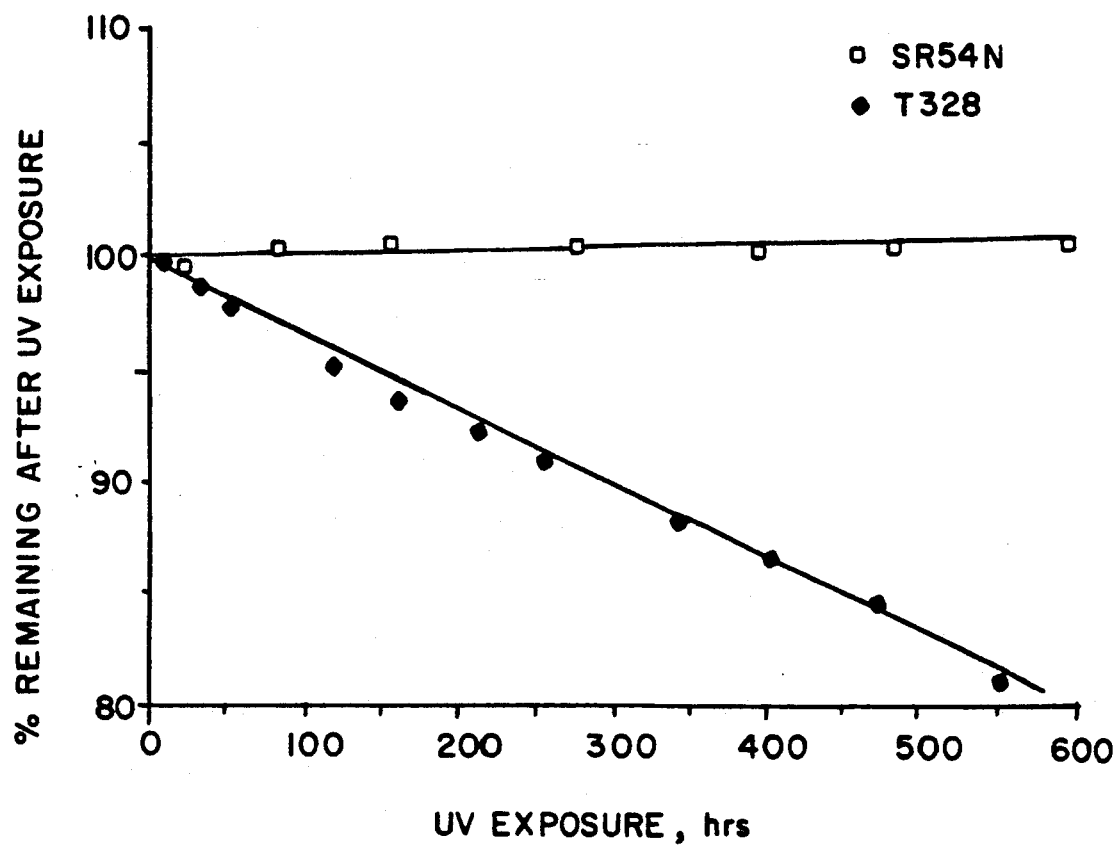
FIG. 3 is a graph showing the stability of a $Ni^{+2}$ complex of 2-(2-pyridyl)benzimidazole/2-ethylhexanoate complex (SR54N) and a 2-(3,5-tert-amyl-6-hydroxyphenyl )benzotriazole (Tinuvin 328) as absorbers of ultraviolet light. Cellulose acetate butyrate was used as the carrier.

EXAMPLE 7—The Use of a $Ni^{+2}$ Complex of 2-(2-pyridyl) benzimidazole/Triphenylphosphine Oxide Complex as an Ultraviolet Absorber The $Ni^{+2}$ complex of 2-(2-pyridyl)benzimidazole/triphenylphosphine oxide complex was dissolved at about 0.5% in a solution of 1:10 cellulose acetate butyrate:ethylacetate and a film was spincoated onto a quartz disc, dried and the initial absorption spectrum of the film was measured. The coated quartz disc was loaded in the carousel of a Rayonet photolysis apparatus and subjected to intense UV radiation for 1000 hours with the absorption spectrum being measured at the time intervals shown in FIG. 2. After each irradiation period, the absorption spectrum was recorded and the loss of ultraviolet absorption was measured at the peak absorbtion wavelength.

This determination required spectral measurements of a reference cellulose acetate butyrate film, and knowledge of the spectral characteristics of the photolysis apparatus, so that the total dose of ultraviolet radiation to the film and the partial dose to the ultraviolet absorber could be calculated. Simultaneously, the same procedure was followed using a commercially available ultraviolet absorber as a standard (e.g., Tinuvin 328 ). The loss of ultraviolet absorption per unit dose of absorbed radiation allows direct comparison of the photochemical stability of tested ultraviolet absorbers.

EXAMPLE 8—The Use of a $Ni^{+2}$ Complex of 2-(2-pyridyl) benzimidazole/Triphenylphosphine Sulfide as an Ultraviolet Absorber The $Ni^{+2}$ complex of 2-(2-pyridyl)benzimidazole/triphenylphosphine sulfide complex was dissolved at about 0.5% in a solution of 1:10 cellulose acetate butyrate:ethylacetate and a film was spincoated onto a quartz disc, dried and the initial absorption spectrum of the film was measured. The coated quartz disc was loaded in the carousel of a Rayonet photolysis apparatus and subjected to intense UV radiation for 1000 hours with the absorption spectrum being measured at the time intervals shown in FIG. 1. After each irradiation period, the absorption spectrum was recorded and the loss of ultraviolet absorption was measured at the peak absorbtion wavelength.

This determination required spectral measurements of a reference cellulose acetate butyrate film, and knowledge of the spectral characteristics of the photolysis apparatus, so that the total dose of ultraviolet radiation to the film and the partial dose to the ultraviolet absorber could be calculated. Simultaneously, the same procedure was followed using a commercially available ultraviolet absorber as a standard (e. g., Tinuvin 328). The loss of ultraviolet absorption per unit dose of absorbed radiation allows direct comparison of the photochemical stability of tested ultraviolet absorbers.

Those skilled in the art will be able to ascertain, using no more than routine experimentation, many equivalents of the specific embodiments of the invention described herein.

These and all other equivalents are intended to be encompassed by the following claims.

We claim:

1. A composition for absorbing ultraviolet light comprising an effective amount of at least one metal complex of a pyridylbenzimidazole compound and a carrier subject to ultraviolet light degradation,
   said pyridylbenzimidazole compound being effective to protect said carrier against ultraviolet light degradation.

2. A composition as claimed in claim 1, further comprising known absorbers.

3. A composition as claimed in claim 1 wherein the pyridylbenzimidazole compound is a 2-(2-pyridyl)benzimidazole compound.

4. A composition as claimed in claim 1 wherein the pyridylbenzimidazole compound is unsubstituted.

5. A composition as claimed in claim 1 which has a maximum absorption at a wavelength between about 250 to 450 nm.

6. A composition as claimed in claim 1 further comprising a solubilizing agent.

7. A compostion as claimed in claim 1 further comprising a stabilizing agent.

8. A composition as claimed in claim 6 wherein the solubilizing agent is also a stabilizing agent.

9. A composition as claimed in claim 6 wherein the solubilizing agent is a surface active agent.

10. A composition as claimed in claim 6 wherein the solubilizing agent is selected from the group consisting of triphenylphosphine oxide, triphenylphosphine sulfide, triphenylphosphine, organic acids, and salts of organic acids.

11. A composition as claimed in claim 7 wherein the stabilizing agent is selected from a group consisting of triphenylphosphine oxide, triphenylphosphine sulfide, organic acids, and salts of organic acids.

12. A composition as claimed in claims 10 or 11 wherein the solubilizing or stabilizing agent is the sodium salt of 2-ethylhexanoic acid.

13. A composition for absorbing ultraviolet light comprising an effective amount of the compound having the following formula:

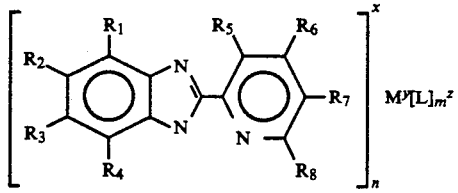

wherein
M is a metal;
L is a ligand;
n is a number between 1 and 4;
m is a number between 0 and 4;
$R_1$-$R_8$ are each is selected from a the group consisting of hydrogen, hydroxyl, alkyl, alkenyl, alkynyl, aryl, aralkyl

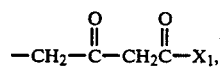

benzimidazoyl, carboxylic acids, carboxylic esters, amides, —$SO_3H$, —$SO_2X_1$; alkylphenols, alkylphenol ethoxylates, halogen, haloalkyl, —$NX_2$, and —$OX_3$, wherein $X_1$ is alkyl, alkenyl, aryl, aralkyl, alkynyl; wherein $X_2$ is hydrogen, oxygen, alkyl, alkenyl, aryl, aralkyl or alkynyl; $X_3$ is hydrogen, alkyl, alkenyl, alkynyl, aryl, aralykyl,

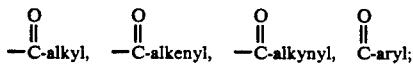

and x, y, and z are the electrical charges associated with the moieties; a carrier, said effective amount of said compound being effective to protect said carrier against ultraviolet light degradation.

14. A composition as claimed in claim 13 wherein x+y+z equals zero.

15. A composition as claimed in claim 13 wherein the pyridylbenzimidazole compound is unsubstituted.

16. A composition as claimed in claim 13 which has a maximum absorption at a wavelength between about 250 to 450 run.

17. A composition as claimed in claim 13 wherein m is greater than zero and L is a solubilizing agent.

18. A composition as claimed in claim 17 further comprising a surface active agent.

19. A composition as claimed in claim 13 wherein m is greater than zero and L is a stabilizing agent.

20. A composition as claimed in claim 17 wherein the solubilizing agent is also a stabilizing agent.

21. A composition as claimed in claim 17 wherein the solubilizing agent is selected from the group consisting of triphenylphosphine oxide, triphenylphosphine sulfide, triphenylphosphine, organic acids, and salts of organic acids.

22. A composition as claimed in claim 19 wherein the stabilizing agent is selected from a group consisting of triphenylphosphine oxide, triphenylphosphine sulfide, organic acids, and salts of organic acids.

23. A composition as claimed in claims 21 or 22 wherein the solubilizing or stabilizing agent is the sodium salt of 2-ethylhexanoic acid.

24. A composition as claimed in claim 13 wherein M is divalent nickel and n is equal to 2.

25. A composition as claimed in claim 13 wherein at least one of $R_1$-$R_8$ is halogen.

26. A composition as claimed in claim 13 wherein at least one of $R_1$-$R_8$ is alkoxy.

27. A composition as claimed in claim 26 wherein the alkoxy is methoxy.

28. A composition as claimed in claim 13 wherein the pyridylbenzimidazole has the following formula:

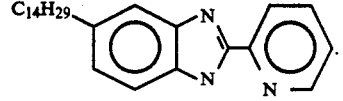

29. A composition as claimed in claim 13 wherein the pyridylbenzimidazole has the following formula:

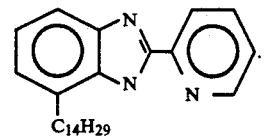

30. A composition as claimed in claim 1 or 9 wherein the pyridylbenzimidazole has the following formula:

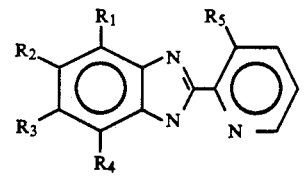

wherein $R_1$-$R_4$ are chloro and $R_5$ is selected from the group consisting of hydrogen, hydroxyl, alkoxy, aryloxy and carboxylic ester.

31. A composition as claimed in claim 30 wherein $R_5$ is hydroxyl.

32. A composition as claimed in claim 30 wherein $R_5$ is methoxy.

33. A composition as claimed in claim 13 wherein the pyridylbenzimidazole comprises the following formula:

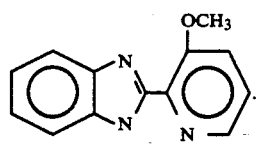

34. A composition as claimed in claim 13 wherein the carrier is a polymeric material.

35. A composition as claimed in claim 34 wherein the polymeric material is a plastic.

36. A composition as claimed in claim 18 wherein the surface active agent is benzalkonium chloride.

* * * * *